United States Patent [19]

Barone et al.

[11] Patent Number: 5,039,518

[45] Date of Patent: Aug. 13, 1991

[54] COSMETIC STICKS

[75] Inventors: Salvatore J. Barone, Staten Island; Ralph A. Macchio, Monsey, both of N.Y.; Julio G. Russ, West Field, N.J.

[73] Assignee: Revlon, Inc., New York, N.Y.

[21] Appl. No.: 567,044

[22] Filed: Jul. 30, 1990

[51] Int. Cl.$^5$ ............................................. A01K 7/021
[52] U.S. Cl. ........................................ 424/63; 424/64; 424/69; 424/DIG. 5
[58] Field of Search ................... 424/63, 64, 69, 65, 424/DIG. 5

[56] References Cited

U.S. PATENT DOCUMENTS

| | | | |
|---|---|---|---|
| 4,606,914 | 8/1986 | Miyoshi | 424/63 |
| 4,648,908 | 3/1987 | Takasuka | 424/69 X |
| 4,659,562 | 4/1987 | Arraudeau | 424/63 |
| 4,710,375 | 12/1987 | Takasuka | 424/69 |
| 4,783,333 | 11/1988 | Mercado | 424/63 |
| 4,795,631 | 1/1989 | Sheehan | 424/64 |
| 4,810,489 | 3/1989 | Murray et al. | 514/938 X |
| 4,837,011 | 6/1989 | Macchio | 424/69 |

FOREIGN PATENT DOCUMENTS 257908 11/1986 Japan.

Primary Examiner—Thurman K. Page
Assistant Examiner—Susan S. Rucker
Attorney, Agent, or Firm—Julie Blackburn

[57] ABSTRACT

A cosmetic stick composition containing PVP/hexadecene copolymer, ester, phenyl trimethicone, spherical silica, bismuth oxychloride, mica, and cosmetic waxes.

6 Claims, No Drawings

5,039,518

COSMETIC STICKS

TECHNICAL FIELD

The invention is directed to cosmetic stick compositions useful as foundation, blush, eyeshadow, anti-perspirant, etc. The sticks contain Polyvinyl Pyrrolidone (PVP)/Hexadecene copolymer, esters, phenyl trimethicone, spherical silica, bismuth oxychloride, mica, and cosmetic waxes.

BACKGROUND OF THE INVENTION

The use of cosmetic sticks to apply cosmetically active ingredients to the skin is well known in the cosmetic art. There are generally three types of cosmetic stick formulations: compressed powder sticks, gel sticks, and wax sticks. Each formulation type has advantages as well as disadvantages over the other forms. For example, compressed powder sticks are often brittle and hard and leave a cosmetically unacceptable dust upon application. Gels, on the other hand, offer excellent aesthetic characteristics but may be unstable due to interaction between the soap gelling agents typically used to solidify the sticks. Wax based sticks are often cosmetically unacceptable because they are hard, greasy and sticky.

There is thus a need for cosmetically stable compositions which are firm enough to resist breakage when applied to the skin, yet perform on the skin like a smooth powder finish without feeling greasy or sticky.

SUMMARY OF THE INVENTION

The invention is directed to cosmetic stick compositions which are easily molded into the desired shapes such as large or small crayons, yet which apply easily to skin without breakage. The cosmetic sticks of the invention leave a very smooth powder film on the skin and, in spite of their wax content, do not feel greasy or heavy.

The invention is directed to a cosmetic stick composition containing a powder phase and an oil phase said powder phase comprising 0.1-15% spherical silica, 0.1-45% bismuth oxychloride, and 0.1-20% mica; and said oil phase comprising 0.30% cosmetic waxes and 0.1-30% ester, 0.1-20% phenyl trimethicone and 0.1-10% PVP/hexadecene copolymer in a 4:2:1 ratio respectively; wherein the percentage of powder phase is 7-11% greater than the percentage of oil phase in the final composition.

This composition provides a cosmetic stick useful as the basis for eyeshadows, blushers, lipsticks, anti-perspirants, moisturizers, foundations, etc. It retains a molded shape, does not easily break upon application of pressure, and performs like a light powder on the skin.

DETAILED DESCRIPTION

The powder phase of the composition essentially contains spherical silica, bismuth oxychloride, and mica and may optionally contain colors and other powder-type fillers. Thus, the term "powder phase" encompasses all of the above constituents as well as any other powder type constituents suitable for inclusion in the composition.

The final composition contains 0.1-15% spherical silica which is considered part of the powder phase. Spherical silica means, in accordance with this invention, a powder of particle size from 2-20 microns which is preferably spherical or nearly spherical in shape. Silica of this type and its preparation are described in Japanese laid-open patent application No. 61-174103 which is hereby incorporated by reference. Spherical silica is also available from a variety of commercial sources including Kobo Products, Inc., Plainfield, N.J.

It is known in the art to treat spherical substances in order to effect surface modifications which enhance the attributes of the material. The spherical silica of the invention may be treated with a variety of materials according to methods well known to those skilled in the art such materials being lecithin, sodium hyaluronate, silicone, teflon, amino acids, sunscreens, isopropyltriisostearyl titanate, polymers such as polyethylene, titanium dioxide, or other suitable materials. For example, U.S. Pat. No. 4,622,074 describes pigments surface treated with lecithin, and U.S. Pat. No. 4,877,604 describes pigments surface treated with titanating agents. Both patents are hereby incorporated by reference.

The final composition also contains 0.1-45% bismuth oxychloride. This material is widely available from a variety of commercial sources. Bismuth oxychloride is an inorganic pigment and filler which enhances the coverage, spreadability and skin adhesion of the final composition.

The final composition contains 0.1-20% mica. This material enhances absorbency and spreadability of the final composition and is available from a number of commercial sources.

The oil phase of the composition contains cosmetic waxes, esters, phenyl trimethicone, and PVP/hexadecene copolymer.

The final composition contains 0.1-30% cosmetic waxes. The waxes provide structure and molding properties and promote skin adhesion. A wide variety of cosmetic waxes are suitable including but not limited to carnauba, ceresin, synthetic, candelilla, microcrystalline, beeswax, parraffin, spermaceti, petrolatum, glyceryl tribehenate, isostearyl behenate, and so on.

Esters comprise 0.1-30% of the final composition. The term "ester" means in accordance with this invention, any ester formed from the reaction of a $C_{4-14}$ acid with an organic alcohol of greater than three carbons, for example, octyl palmitate, glyceral trioctanoate, isostearyl neopentanoate, isopropyl palmitate, 2-ethylhexyl palmitate, isobutyl palmitate, isopropyl isostearate, octyl stearate, glycerol octanoate, neopentyl glycol diisooctanoate, isostearyl palmitate, and so on.

The composition also contains 0.1-20% phenyl trimethicone also known as phenyl dimethicone. This material is widely available from commercial sources such as Dow Corning.

Finally the composition essentially contains 0.1-10% PVP/hexadecene copolymer. Although the range of each ingredient may vary, it is essential that the ratio of ester: phenyl trimethicone: PVP hexadecene copolymer is approximately 4:2:1 respectively in the final composition. It is also necessary that the percentage of powder phase is 7-11% greater than the percentage of oil phase in the final composition.

As mentioned previously the composition may contain optional ingredients which form part of the powder or oil phases so long as the ratio and percentage of powder and oil phases remains as set forth above. For example, in the preferred embodiment of the invention colors and other fillers form part of the powder phase. For example, the final composition may consist of 0.1-40% colors and 0.1-15% fillers in addition to the aforementioned essential constituents of the powder phase. A wide variety of colors may be used and they may be treated or untreated. It is known in the art to treat pigments to effect surface modifications which enhance color attributes, or add certain benefits, such as to decrease surface tension, increase adherence, and so on. Pigments may be coated with substances such as silicone, teflon, etc. as mentioned previously. Suitable colors are organic or inorganic pigments which are either treated or untreated. Inorganic pigments such as black, yellow, and red iron oxides, amber, ultramarine, chromium oxide, ferric ferrcyanide and so on are suitable. Suitable organic pigments are all FDA approved D&C and FD&C colors.

The preferred embodiment of the invention also contains 0.1–15% of other powder phase fillers such as N-lauryl-L-lysine, titanium dioxide, zinc oxide, kaolin, magnesium oxide, magnesium carbonate, etc.

The preferred embodiment of the invention contains the following ranges of essential constituents:

| | |
|---|---|
| 3–7% | PVP/hexadecene copolymer |
| 15–25% | ester |
| 5–15% | phenyl trimethicone |
| 6–10% | spherical silica |
| 14–18% | bismuth oxychloride |
| 5–10% | mica |
| 1.0–2.0% | carnauba wax |
| 1.0–2.0% | ceresin |
| 3.0–4.6% | synthetic wax |

The preferred embodiment also contains 1–5% of a filler, most preferably N-lauryl-L-lysine and 14–18% colors. The preferred ester is glycerol trioctanoate.

The cosmetic stick compositions of the invention are made by first blending the dry ingredients. The blended dry ingredients are then poured into the molten wax phase. The composition is poured into the desired molds and allowed to cool.

The invention will be further described in connection with the following examples which are set forth for the purposes of illustration only.

EXAMPLE 1

| Eyeshadow Crayon | % |
|---|---|
| Carnauba wax | 1.450 |
| Ceresin | 1.450 |
| Synthetic wax | 3.800 |
| Methylparaben | 0.300 |
| Propylparaben | 0.100 |
| BHA | 0.100 |
| PVP/hexadecene copolymer | 5.100 |
| PEG-14 diheptanoate | 3.400 |
| Glyceryl trioctanoate | 26.000 |
| Phenyl trimethicone | 10.200 |
| Red iron oxide | 7.800 |
| Yellow iron oxide | 11.500 |
| Black iron oxide | 1.800 |
| Mica | 7.000 |
| Talc | 0.001 |
| Silica | 1.999 |
| N-lauryl Lysine | 2.000 |
| Bismuth Oxychloride (BIOCL) | 16.000 |

EXAMPLE 2

A free-standing make-up or concealer crayon was formulated as set forth below:

| | % |
|---|---|
| Carnauba wax | 1.450 |
| Ceresin wax | 1.450 |
| Synthetic wax | 3.800 |
| Methyl paraben | 0.300 |
| Propyl paraben | 0.100 |
| BHA | 0.100 |
| PVP/hexadecene copolymer | 5.100 |
| PEG-4-diheptanoate | 3.400 |
| Glyceryl trioctanoate | 26.000 |
| Phenyl dimethicone | 10.200 |
| Red iron oxide | 1.500 |
| Yellow iron oxide | 2.700 |
| Black iron oxide | 0.350 |
| Mica | 7.000 |
| Talc | 2.550 |
| TiO$_2$ | 8.000 |
| Silica | 8.000 |
| N-lauryl Lysine | 2.000 |
| BIOCL | 16.000 |

EXAMPLE 3

A free standing lipstick/blush was formulated as set forth below:

| | % |
|---|---|
| Carnauba wax | 1.450 |
| Ceresin wax | 1.450 |
| Synthetic wax | 3.800 |
| Methyl paraben | 0.300 |
| Propyl paraben | 0.100 |
| BHA | 0.100 |
| PVP/hexadecene copolymer | 5.100 |
| PEG-4-Diheptanoate | 3.400 |
| Glyceryl Tri-octanoate | 26.000 |
| Phenyl trimethicone | 10.200 |
| FD & C Yellow #5 | 0.180 |
| D & C Red.#7 | 0.450 |
| Mica | 7.000 |
| Talc | 14.470 |
| Silica | 8.000 |
| N-lauryl-L-lipsine | 2.000 |
| BIOCL | 16.000 |

While the invention has been described in connection with the preferred embodiment it is not intended to limit the scope of the invention to the particular form set forth but, on the contrary, it is intended to cover such alternatives, modifications, and equivalents as may be included within the spirit and scope of the appended claims.

We claim:

1. A composition containing a powder phase and an oil phase said powder phase comprising 0.1–15% spherical silica, 0.1–45% bismuth oxychloride, and 0.1–20% mica; and said oil phase comprising 0.30% cosmetic waxes and 0.1–30% ester, 0.1–20% phenyl trimethicone, and 0.1–10% PVP/hexadecene copolymer in a 4:2:1 ratio respectively; wherein the percentage of powder phase is 7–11%. greater than the percentage oil phase in the final composition.

2. The composition of claim 1 wherein the powder phase additionally contains 0.1–15% fillers.

3. The composition of claim 2 wherein the powder phase additionally contains 0.1–40% colors.

4. The composition of claim 2 containing 6–10% spherical silica, 14–18% bismuth oxychloride, 5–10% mica, 1.0–2.0% carnauba wax, 1.0–2.0% ceresin, 3.0–4.6 synthetic wax, 15–25% ester, 5–15% phenyl trimethicone, and 3–7% PVP/hexadecene copolymer.

5. The composition of claim 3 containing 1–5% fillers and 14–18% colors.

6. The composition of claim 4 wherein the ester is glycerol trioctanoate.

* * * * *